United States Patent [19]

Dürsch et al.

[11] 4,267,125

[45] May 12, 1981

[54] PROCESS FOR THE MANUFACTURE OF PHOSPHINIC AND PHOSPHONIC ACID ANHYDRIDES

[75] Inventors: Walter Dürsch, Königstein; Hans-Jerg Kleiner, Kronberg, both of Fed. Rep. of Germany

[73] Assignee: Hoechst Aktiengesellschaft, Fed. Rep. of Germany

[21] Appl. No.: 125,183

[22] Filed: Feb. 27, 1980

[30] Foreign Application Priority Data

Mar. 2, 1979 [DE] Fed. Rep. of Germany ....... 2908264

[51] Int. Cl.$^3$ .............................................. C07F 9/02
[52] U.S. Cl. ................................ 260/545 P; 260/988
[58] Field of Search ...................... 260/545 P, 988, 933

[56] References Cited

U.S. PATENT DOCUMENTS

| 3,639,473 | 2/1972 | Venezky .......................... 260/545 P |
| 4,196,141 | 4/1980 | Kleiner et al. ................... 260/545 P |

*Primary Examiner*—Anton H. Sutto
*Attorney, Agent, or Firm*—Connolly and Hutz

[57] ABSTRACT

Process for the manufacture of phosphinic and phosphonic acid anhydrides by reacting phosphinic and phosphonic acid halides with an aliphatic carboxylic acid anhydride and removing the carboxylic acid halide having been formed by distillation.

1 Claim, No Drawings

PROCESS FOR THE MANUFACTURE OF PHOSPHINIC AND PHOSPHONIC ACID ANHYDRIDES

It has already been well-known to prepare phosphinic and phosphonic acid anhydrides by reacting phosphinic and phosphonic acid halides with molar amounts of water or with molar amounts of free phosphinic or phosphonic acids. This process is especially important in those cases where the halides may be obtained more easily than for example the esters or the free acids. However, said process yields considerable amounts of gaseous hydrogen halides, which must be absorbed in a complicated operation and, if required, must be removed by neutralization.

There has now been found a simplified process starting from phosphinic and phosphonic acid halides for the manufacture of phosphinic and phosphonic acid anhydrides of the formula

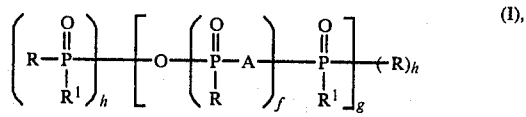

in which
A stands for alkylene, aralkylene or arylene with 1 to 10 carbon atoms each,
R is $C_1$–$C_3$-alkyl,
$R^1$ is $C_1$–$C_{18}$-alkyl or alkenyl which may be substituted by fluorine, chlorine or bromine and may be interrupted by ether oxygen atoms; cycloalkyl or alkylcycloalkyl of a total of 1 to 10 carbon atoms each; aryl or alkylaryl optionally being substituted in the ring by chlorine and/or bromine;
f is 0 or 1, preferably 0, and always 0 if h is 1;
g is 1, if h is 1 and f is 0 at the same time, or if h is 0, f is 1 and A is $C_3H_6$;
g is 3 to formally infinite, if h and f are 0, and
g is 2 to formally infinite, if h is 0, f is 1 and A is other than $C_3H_6$, and
h is 0 or 1, preferably 0.

These compounds are obtained according to the invention by reacting one mol of a compound of the formula

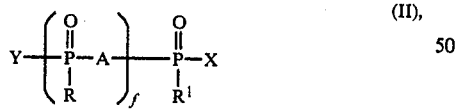

in which X is chlorine or bromine, preferably chlorine, Y is defined as R and is additionally defined as X, and R, $R^1$, A and f are defined as in the above formula I, with at least b/2 mol(s) of an aliphatic carboxylic acid anhydride of the formula $$(R^2-CO-)_2-O \quad (III),$$

b being the number of the halogen atoms in the compound of the formula I and $R^2$ being $C_1$–$C_3$-alkyl, chloromethyl, dichloromethyl or trichloromethyl, preferably $CH_3$ and $C_2H_5$, and removing the carboxylic acid halides being formed as by-products by distillation.

The invention relates in particular to the preparation of those compounds of the formula I, in which A is $C_1$–$C_6$-alkylene, xylylene, phenylene or a group of the formula

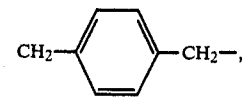

R is $C_1$–$C_3$-alkyl, $R^1$ is $C_1$–$C_4$-alkyl or alkenyl, especially $C_1$–$C_3$-alkyl, phenyl or benzyl, and f, g and h are defined as above.

The phosphinic and phosphonic acid halides of the formula I which are suitable for the reactions may be divided into three groups.

1st group: Mono-phosphinic acid halides of the formula $I_M$

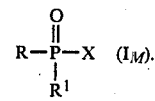

Of these, there may be mentioned, for example: Tetradecyl-methyl-phosphinic acid chloride, di-n-octyl-phosphinic acid chloride, di-n-butyl-phosphinic acid chloride, di-i-propyl-phosphinic acid chloride, di-ethyl-phosphinic acid chloride, and preferably methyl-propyl-phosphinic acid chloride, methyl-ethyl-phosphinic acid chloride, di-methylphosphinic acid chloride, methyl-vinyl-phosphinic acid chloride, methyl-chloromethyl-phosphinic acid chloride.

2nd group: 1, ω-Alkane-bis-(alkyl-phosphinic acid halides) of the formula $I_B$

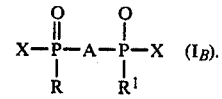

Of these, there may be mentioned, for example: 1,4-n-butane-bis-(n-butyl-phosphonic acid bromide), 1,6-n-hexane-bis-(ethyl-phosphinic acid chloride), 1,8-n-octane-bis-(n-propyl-phosphinic acid chloride), and preferably all compounds of the formula $I_{B,b}$

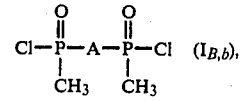

in which A is $C_1$–$C_{10}$-alkylene. Particularly preferred are those compounds in which A represents $CH_2$, $C_2H_4$ or $C_6H_{12}$.

3rd group- Phosphonic acid halides of the formula $I_Z$

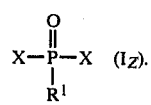

Of these, there may be mentioned, for example: Phenyl-methane-phosphonic acid dibromide, benzene-phosphonic acid chloride, cyclohexane-phosphonic acid dichloride, hexadecane-phosphonic acid dichloride, dodecane-phosphonic acid dichloride, n-octane-phosphonic acid dichloride, n-hexane-phosphonic acid dichloride, isobutane-phosphonic acid dichloride, preferably propane-phosphonic acid dichloride, ethane-phosphonic acid dichloride, chloromethane-phosphonic acid dichloride and in particular methane-, ethane- and n-propane-phosphonic acid dichloride.

It is of course also possible to use mixtures of different compounds of the formula I.

Suitable carboxylic acid anhydrides of formula I are, for example:

Trichloroacetic acid anhydride, chloroacetic acid anhydride, butyric acid anhydride, preferably acetic anhydride and especially propionic acid anhydride, since this latter anhydride helps to avoid the formation of dark-colored by-products. There may also be used mixtures of different carboxylic acid anhydrides of formula II.

The molar ratios of the phosphinic and phosphonic acid anhydrides of formula I and the aliphatic carboxylic acid anhydrides of formula II are in the range of from about 1:0.8 to 1:10, preferably from 1:0.95 to 1:3. The reactants are suitably mixed at room temperature with the exclusion of moisture and air and heated together at normal pressure or in a slight vacuum. It is also possible, however, to heat first component I and then to add component II dropwise, and vice versa. The reaction temperatures are in the range of from 30° to 160° C., preferably from 60° to 130° C. In order to avoid possible discolorations, it is recommended at first not to exceed a temperature of from 90° to 110° C. for those halides which do not immediately react already at 90° to 110° C., while splitting off carboxylic acid halides. Also with less reactive halides of the formula I, the reaction slowly starts already at 80° to 110° C. When acetic anhydride is employed, there is a gradually increasing reflux of acetyl chloride (boiling point 51° C.) after about 10 to 300 minutes, preferably 30 to 120 minutes. It is recommended to remove the acetyl chloride having been formed by distillation optionally via a column not until said reflux has become strong enough, thus reducing the internal temperature of the reaction mixture. On the other hand, it is also possible to distill the acetyl chloride off immediately in the same measure as it is being formed, by way of a column. The reaction periods including the elimination of the carboxylic acid chloride by distillation may vary—depending on the type of the halides of the formula I—from 10 minutes to 20 hours, preferably from 1 to 8 hours.

If use was made of an excess amount of carboxylic acid anhydrides of the formula II, said excess must also be removed by distillation after distilling off the lower-boiling carboxylic acid halides. This should suitably be executed in a rather high vacuum at the lowest possible internal temperatures, to avoid discolorations.

The phosphinic and phosphonic acid anhydrides remaining as distillation residues are obtained in a pure state and in a practically quantitative yield. This is particularly true, if the carboxylic acid anhydride is employed in more or less large excess amounts which are carefully removed by distillation. Acid catalysts, for example tin tetrachloride, aluminum chloride or boron trifluoride etherate, accelerate the reaction. However, they involve impurities and partly also undesirable discolorations, so that their use should be checked from case to case. It is a remarkable fact with regard to the present process that no mixed anhydrides are formed of the phosphorus-containing acids and the carboxylic acids.

The phosphorus-containing anhydrides obtained in the present process represent important intermediates. By means of simple reactions, for example with ethylene oxide, valuable flame retardants may be obtained, as they have been described, for example, in German Offenlegungsschrift No. 2,726,478. Other simple reactions, for example with water to yield the corresponding phosphorus-containing acids, lead to important phosphorus-containing intermediates and final products which are widely used for example in the fields of dyestuffs, dyeing auxiliaries and corrosion inhibitors.

The following Examples illustrate the invention.

EXAMPLE 1

200 Grams (1.24 mols) of propane-phosphonic acid dichloride and 126.5 g (1.24 mols) of acetic anhydride are mixed and heated to 100° to 120° C., while stirring. After 1 hour, acetyl chloride starts to distill off via a column. After 7 hours, 176 g of acetyl chloride have been distilled off. Subsequently the distillation is carried out at 30 torrs up to an internal temperature of 120° C. In a cooled receiver there are collected 19 g of acetyl chloride (176+19 g=195 g=2.48 mols). There remain 132 g of propane-phosphonic acid anhydride having a chloride content of 0.3%. This corresponds to a yield of 100% of the theory.

EXAMPLE 2

200 Grams (1.24 mols) of propane-phosphonic acid dichloride and 253 g (2.48 mols) of acetic anhydride are mixed and heated to 100° to 115° C., while stirring. After 1 hour, acetyl chloride starts to distill off via a column. After 4.5 hours, 176 g of acetyl chloride have been distilled off. Subsequently the distillation is executed, while applying a water jet vacuum, up to an internal temperature of 100° C. Excess acetic acid chloride is distilled off. In a cooling trap superposed to the pump there are collected 19 g of acetyl chloride (176+19 g=195 g=2.48 mols). The distillation residue is distilled at 2 torrs up to an internal temperature of 150° C. There remain 131.5 g of propane-phosphonic acid anhydride free from chloride. This corresponds to a yield of 100% of the theory.

If the process is carried out in the same manner, however, with the addition of 1% of tin tetrachloride or 0.5% of boron trifluoride etherate as catalyst, the reaction is considerably accelerated and the total amount of acetyl chloride has already been distilled off after 2 hours. However, in this case the distillation residue shows a strong discoloration.

EXAMPLE 3

210 Grams (1.035 mols) of n-hexane-phosphonic acid dichloride and 211 g (2.07 mols) of acetic anhydride are mixed and heated to 90° to 100° C., while stirring. After 40 minutes, acetyl chloride starts to distill off via a column. Within 3 hours the internal temperature is increased to 120° C. At that point 137 g of acetyl chloride have been distilled off altogether. Thereafter the excess acetic anhydride is distilled off in the water jet vacuum up to an internal temperature of 100° C. In a cooling trap superposed to the pump there are collected 26 g of acetyl chloride (137 g+26 g=163 g=2.07 mols). The distillation residue is distilled at 2 torrs up to an internal temperature of 120° C. There remain 154 g of n-hexane-phosphonic acid anhydride free from chloride. This corresponds to a yield of 100% of the theory.

EXAMPLE 4

126 Grams (1 mol) of ethylmethyl-phosphinic acid chloride and 102 g (1 mol) of acetic anhydride are mixed and heated to 90° C., while stirring. Acetyl chloride distills off via a column. After 2 hours, 60 g of acetyl chloride have been distilled off with a simultaneous gradual increase of the internal temperature to 120° C. Finally the distillation is carried out in the water jet vacuum to remove excess acetic anhydride, up to an internal temperature of 120° C. In a cooling trap superposed to the pump there remain 19 g of acetyl chloride (60 g+19 g=79 g=1 mol). Subsequently the distillation is carried out at 1 torr up to an internal temperature of 135° C. There remain 900 g of ethylmethyl-phosphinic acid anhydride free from chloride. This corresponds to a yield of 100% of the theory.

EXAMPLE 5

100 Grams (0.805 mol) of methylvinyl-phosphinic acid chloride and 164 g (1.61 mols) of acetic anhydride are mixed and heated to 100° C., while stirring. Acetyl chloride distills off via a column. The temperature is gradually increased to 120° C. within 2 hours. In the course of this process, 46 g of acetyl chloride are distilled off. Thereafter the distillation is effected in the water jet vacuum to remove the excess acetic anhydride, up to an internal temperature of 120° C. In a cooling trap superposed to the pump there remain 17 g of acetyl chloride (46 g+17 g=63 g=0.805 mol), Subsequently the distillation is carried out at 2 torrs up to an internal temperature of 130° C. There remain 79 g of methylvinyl-phosphinic acid anhydride free from chloride. This corresponds to a yield of 100% of the theory.

EXAMPLE 6

143 Grams (0.735 mol) of benzene-phosphonic acid dichloride and 149.5 g (1.47 mol) of acetic anhydride are mixed and heated to 90°–115° C., while stirring. After 1 hour acetyl chloride starts to distill off via a column. After another 3 hours the removal of the acetyl chloride by distillation has been completed. The distillation is then carried out in the water jet vacuum up to an internal temperature of 130° C., thereafter at 2 torrs up to an internal temperature of 120° C. There remain 103 g of benzenephosphonic acid anhydride free from chloride. This corresponds to a yield of 100% of the theory.

EXAMPLE 7

44.4 Grams (0.2 mol) of 1.2-ethane-bis-(methyl-phosphinic acid chloride) and 40.8 g (0.4 mol) of acetic anhydride are heated to 80° C. In this process an intense reflux of acetyl chloride is found already after 10 minutes. Within one hour 25 g (0.319 mol) of acetyl chloride are distilled off. A vacuum of 120 mbars at first and later of 30 mbars is applied, and the internal temperature is increased to 153° C. In the course of this process another 6 g (0.077 mol) of acetyl chloride and 20 g of acetic anhydride are distilled off into a cooling trap. There remain 34 g of glass-like 1,2-ethane-bis-(methyl-phosphinic acid) anhydride being free from chlorine. (Theory: 33.6 g).

EXAMPLE 8

59.0 Grams (0.2 mol) of tetradecyl-methyl-phosphinic acid chloride and 51 g (0.5 mol) of acetic anhydride are heated to 80° C. Already after 20 minutes acetyl chloride is formed. Within 60 minutes 13 g (0.166 mol) of the same are distilled off. After the application of a vacuum of 20 mbars, another 2.5 g (0.032 mol) of acetyl chloride and 30 g of acetic anhydride are distilled off into a cooling trap. There remain 53 g (theory=53.4 g) of tetradecyl-methylphosphinic acid anhydride being free from chlorine.

EXAMPLE 9

83.7 Grams (0.5 mol) of chloromethane-phosphonic acid dichloride and 61.2 g (0.6 mol) of acetic anhydride are heated to 60° C. At an internal temperature of from 55° to 57° C. there is immediately a reflux of acetyl chloride. After one hour the acetyl chloride having been formed is distilled off for the most part first at normal pressure and then at 40 mbars. By applying a vacuum of 1 mbar, another 5 g of acetyl chloride and 10 g of acetic anhydride are removed at 75° C. There remain 55 g (=about 98% of the theory) of chloride-free chloromethane-phosphonic acid anhydride.

EXAMPLE 10

72.5 Grams (0.5 mol) of vinyl-phosphonic acid dichloride and 61.2 g (0.6 mol) of acetic anhydride are heated to 107° C. In the course of this process there is a slight reflux of acetyl chloride. After 5 hours the internal temperature has dropped to 60° C. due to the increasingly strong formation of acetyl chloride. After removing the main portion (76 g) of the acetyl chloride formed by distillation at first at normal pressure, and then at 35 mbars, and removing the remainder of acetyl chloride (2 g) and the excess acetic anhydride (10 g) at 1 mbar and 90° C., there remain 46 g of vinyl-phosphonic acid anhydride free from chloride (theory: 45 g).

EXAMPLE 11

61.5 grams (0.5 mol) of methane-phosphonic acid dichloride and 61.2 g (0.6 mol) of acetic anhydride are heated to 75° C. In the course of this process there is a reflux of acetyl chloride. After 150 minutes the internal temperature has dropped to 58° C. due to the gradually increasing formation of acetyl chloride. After the removal of all volatile portions by distillation first at normal pressure, then at 30 mbars and finally at 1 mbar and at internal temperatures of 60° to 80° C., there remain as residue 38 g (theory: 39 g) of methane-phosphonic acid anhydride free from chloride.

EXAMPLE 12

64.4 Grams (0.6 mol) of propane-phosphonic acid dichloride and 65.1 g (0.5 mol) of propionic acid anhydride are heated to 100° C. After 20 minutes a strong acid anhydride propionic acid dichloride (boiling point 80° C.) sets in. The mixture is continued to be heated for another hour. In this process the internal temperature drops to 88° C. due to the gradually increasing reflux. At a temperature of up to 105° C. 58 g (0.60 mol) of propionic acid chloride are distilled off via a small column. A water jet vacuum of 28 mbars is applied, and at a temperature of up to 150° C. there are distilled further 10 g of propionic acid chloride (0.65 mol) into a cooling trap as well as 6 g of propionic acid chloride (0.088 mol) and 11.5 g (0.108 mol) of propionic acid anhydride into the distillation receiver. By applying in oil pump vacuum of 1 mbar at 150° C., another 1.5 g (0.011 mol) of propionic acid anhydride are eliminated. There remain 42.5 g (theory: 42.4 g) of propane-phosphonic acid anhydride being free from chlorine.

What is claimed is:

1. Process for the manufacture of phosphinic and phosphonic acid anhydrides of the formula

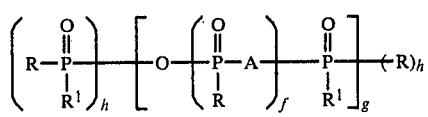 (I), in which
- A stands for alkylene, aralkylene or arylene with 1 to 10 carbon atoms each,
- R is $C_1$-$C_8$-alkyl,
- $R^1$ is $C_1$-$C_{18}$-alkyl or alkenyl which may be substituted by fluorine, chlorine or bromine and may be interrupted by ether oxygen atoms; cycloalkyl or alkylcycloalkyl of a total of 1 to 10 carbon atoms each; aryl or alkylaryl optionally being substituted in the ring by chlorine and/or bromine;
- f is 0 ot 1, preferably 0, and always 0 if h is 1;
- g is 1, if h is 1 and f is 0 at the same time, or if h is 0, f is 1 and A is $C_3H_6$;
- g is 3 to formally infinite, if h and f are 0, and
- g is 2 to formally infinite, if h is 0, f is 1 and A is other than $C_3H_6$, and
- h is 0 or 1, preferably 0, which comprises reacting at 30°–160° C. one mol of a compound of the formula

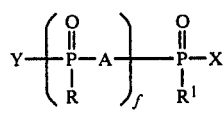 (II), in which X is chlorine or bromine, preferably chlorine, Y is defined as R and is additionally defined as X, and R, $R^1$, A and f are defined as in the above formula I, with at least b/2 mol(s) of an aliphatic carboxylic acid anhydride of the formula

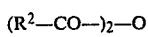 (III), b being the number of the halogen atoms in the compound of the formula I and $R^2$ being $C_1$-$C_3$-alkyl, chloromethyl, dichloromethyl or trichloromethyl, preferably $CH_3$ and $C_2H_5$, and removing the carboxylic acid halides being formed as by-products by distillation.

* * * * *